United States Patent [19]

Cohan et al.

[11] Patent Number: 5,696,141
[45] Date of Patent: Dec. 9, 1997

[54] ISOXAZOLINE COMPOUNDS AS 5-LIPOXYGENASE INHIBITORS

[75] Inventors: Victoria Lee Cohan, East Lyme; Edward Fox Kleinman, Stonington, both of Conn.

[73] Assignee: Pfizer Inc., New York, N.Y.

[21] Appl. No.: 700,432

[22] PCT Filed: Jan. 19, 1995

[86] PCT No.: PCT/IB95/00041

§ 371 Date: Sep. 5, 1996

§ 102(e) Date: Sep. 5, 1996

[87] PCT Pub. No.: WO95/24192

PCT Pub. Date: Sep. 14, 1995

Related U.S. Application Data

[63] Continuation of Ser. No. 208,768, Mar. 9, 1994, abandoned.

[51] Int. Cl.$^6$ ................................. A61K 31/42
[52] U.S. Cl. ................ 514/378; 514/379; 514/380
[58] Field of Search ............... 514/378, 379, 514/380

[56] References Cited

U.S. PATENT DOCUMENTS

| 4,731,382 | 3/1988 | Zusi et al. ............... 514/575 |
| 4,889,551 | 12/1989 | Oda et al. ............... 548/240 |
| 5,059,614 | 10/1991 | Lepage et al. ............ 514/378 |
| 5,208,251 | 5/1993 | Belliotti et al. .......... 514/372 |
| 5,234,937 | 8/1993 | Capiris et al. ........... 514/374 |
| 5,288,397 | 2/1994 | Lepage et al. ............ 514/380 |

FOREIGN PATENT DOCUMENTS

| 0247725 | 12/1987 | European Pat. Off. . |
| 0378991 | 7/1990 | European Pat. Off. . |
| 0401903 | 12/1990 | European Pat. Off. . |
| 9107178 | 5/1991 | WIPO . |
| 9108202 | 6/1991 | WIPO . |
| 9115451 | 10/1991 | WIPO . |
| 9207567 | 5/1992 | WIPO . |
| 9219589 | 11/1992 | WIPO . |
| 9219594 | 11/1992 | WIPO . |
| 9402448 | 2/1994 | WIPO . |
| 9418158 | 8/1994 | WIPO . |

OTHER PUBLICATIONS

H. Masamune and L. S. Melvin, Jr., Annual Reports in Medicinal Chemistry, 24, 71–80, Academic Press, 1989.
Derwent Publications AN 91-329223 abstract of JP, A, 03 220 180 (1991).
Arzneim.–Forsch. vol. 24, No. 4, 1974, pp. 494–499.
J. Org. Chem., vol. 37, No. 19, 1972, cis–8, 9–Dihydroisoxazolo [5,4–d] pyrimidine–4, 6(5H,7H)–diones, Tuman et al., pp. 2983–2986.
CA 77: 139965b, cis–8, 9–. . .–diones, Tuman et al., p. 441, 1972.
CA 112: 198215w Substitution . . . derivatives. Badr et al., p. 699, 1990.
CA 112: 216875t Synthesis . . . triazines. Badr et al., pp. 639–640, 1990.

*Primary Examiner*—Theodore J. Criares
*Attorney, Agent, or Firm*—Peter C. Richardson; Gregg C. Benson; A. Dean Olson

[57] ABSTRACT

This invention relates to a method of inhibiting 5-lipoxygenase in a mammal in need thereof by administering compounds of the core of formula

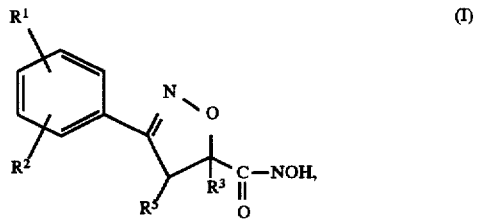

(I)

the racemic, racemic-diastereomeric mixtures and optical isomers of said compounds and the pharmaceutically acceptable salts thereof.

4 Claims, No Drawings

ISOXAZOLINE COMPOUNDS AS 5-LIPOXYGENASE INHIBITORS

CROSS REFERENCE TO RELATED APPLICATIONS

This application is the national stage of International application Ser. No. PCT/IB95/00041, filed Jan. 19, 1995, designating, inter alia, the United States which is a continuation of U.S. application Ser. No. 08/208,768, filed Mar. 9, 1994, now abandoned.

BACKGROUND OF THE INVENTION

This invention relates to a method of inhibiting 5-lipoxygenase (5-LO) in a mammal in need thereof which comprises administering to said mammal a 5-lipoxygenase inhibiting amount of a compound of the formula (I), shown below, or a pharmaceutically acceptable salt thereof, and as such are useful in the treatment or alleviation of inflammatory disease or condition, allergy and cardiovascular diseases in mammals wherein the inflammatory disease or condition is asthma, arthritis, bronchitis, chronic obstructive pulmonary disease, psoriasis, allergic rhinitis, dermatitis, shock, atopic dermatitis, rheumatoid arthritis or osteoarthritis; and this invention also relates to pharmaceutical compositions useful therefor.

Arachidonic acid is known to be the biological precursor of several groups of endogenous metabolites, prostaglandins including prostacyclins, thromboxanes and leukotrienes. The first step of arachidonic acid metabolism is the release of esterified arachidonic acid and related unsaturated fatty acids from membrane phospholipids via the action of phospholipase. Free fatty acids are then metabolized either by cycloxygenase to produce the prostaglandins and thromboxanes or by lipoxygenase to generate hydroperoxy fatty acids which may be further converted to leukotrienes. Leukotrienes have been implicated in the pathophysiology of inflammatory diseases, including rheumatoid arthritis, gout, asthma, ischemia, reperfusion injury, psoriasis and inflammatory bowel disease. Any drug that inhibits lipoxygenase is expected to provide significant new therapy for both acute and chronic inflammatory conditions.

Recently, several review articles on lipoxygenase inhibitors have been reported. See, for example, H. Masamune and L. S. Melvin, Sr., in *Annual Reports in Medicinal Chemistry*, 24, 71–80 (Academic Press, 1989) and B. J. Fitzsimmons and J. Rokach in Leukotrienes and Upoxygenases, 427–502 (Elsevier, 1989).

The compounds utilized in the present invention are disclosed and claimed in copending U.S. application Ser. No. 08/157,248 filed Nov. 26, 1993 and Ser. No. 08/157,241 filed Nov. 26, 1993, wherein said compounds are disclosed as having phosphodiesterase type IV ($PDE_{IV}$) inhibiting activity. The disclosures thereof are incorporated herein by reference.

SUMMARY OF THE INVENTION

This invention is concerned with a method of inhibiting production of 5-lipoxygenase (5-LO) in a mammal in need thereof which method comprises administering to said mammal an effective amount of a compound selected from the group consisting of compounds of the formula (I)

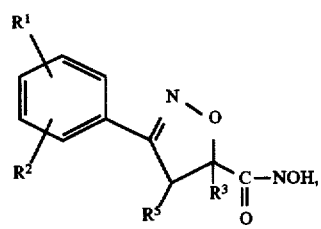

the racemic, racemic-diastereomeric mixtures and optical isomers of said compounds, and the pharmaceutically acceptable salts thereof, wherein $R^1$ is —O($C_1$–$C_4$)alkyl, —O($CH_2$)$_n$phenyl where the phenyl portion is optionally substituted with ($C_1$–$C_4$)alkyl, ($C_1$–$C_4$)alkoxy, halogen or $CF_3$, or —O($CH_2$)$_n$quinoline where the quinoline is optionally substituted with ($C_1$–$C_4$)alkyl, ($C_1$–$C_4$)alkoxy, halogen or $CF_3$;

n is 0 or an integer from 1 to 6;

$R^2$ is hydrogen, —O($C_1$–$C_4$)alkyl, —O($C_3$–$C_7$)cycloalkyl or —O($CH_2$)$_n$phenyl where the phenyl portion is optionally substituted with ($C_1$–$C_4$)alkyl, ($C_1$–$C_4$)alkoxy, halogen or $CF_3$;

$R^3$ is hydrogen or ($C_1$–$C_4$)alkyl;

$R^4$ is hydrogen or ($C_1$–$C_4$)alkyl; and $R^5$ is hydrogen or ($C_1$–$C_4$)alkyl; provided that when:

$R^1$, $R^3$, $R^4$, and $R^5$ are each hydrogen $R^2$ is not 3-O-cyclopentyl;

$R^3$, $R^4$, and $R^5$ are each hydrogen and $R^2$ is 3-OMe, $R^1$ is not 4-O-cyclopentyl; and $R^4$ and $R^5$ are each hydrogen, $R^3$ is ethyl, $R^1$ is 4-OMe, $R^2$ is not 3-O-($CH_2$)$_5$phenyl.

A preferred method of inhibiting production of 5-lipoxygenase (5-LO) in a mammal in need thereof which method comprises administering to said mammal an effective amount of a compound selected from the group consisting of compounds of the formula (I)

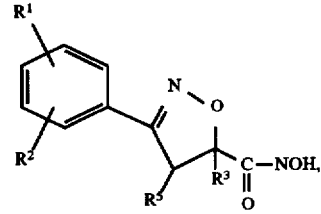

the racemic, racemic-diastereomeric mixtures and optical isomers of said compounds, and the pharmaceutically acceptable salts thereof, wherein $R^1$ is 4-OMe, 4-O-$CH_2$-phenyl or 4-O-$CH_2$-2-quinoline;

$R^2$ is hydrogen, 3-O-cyclopentyl or 3-O($CH_2$)$_5$phenyl;

$R^3$ is hydrogen, methyl or ethyl;

$R^4$ is hydrogen or methyl; and $R^5$ is hydrogen;

provided that when:

$R^4$ and $R^5$ are each hydrogen, $R^3$ is ethyl, $R^1$ is 4-OMe, $R^2$ is not 3-O-($CH_2$)$_5$phenyl.

Further, this invention is directed to a method of treating or alleviating an inflammatory disease or condition, allergy or cardiovascular disease in a mammal in need thereof which method comprises administering to said mammal an effective amount of a compound selected from the group consisting of compounds of the formula (I)

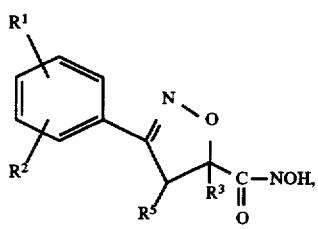

(I)

the racemic, racemic-diastereomeric mixtures and optical isomers of said compounds, and the pharmaceutically acceptable salts thereof, wherein $R^1$ is —O($C_1$–$C_4$)alkyl, —O($CH_2$)$_n$phenyl where the phenyl portion is optionally substituted with ($C_1$–$C_4$)alkyl, ($C_1$–$C_4$)alkoxy, halogen or $CF_3$, or —O($CH_2$)$_n$quinoline where the quinoline is optionally substituted with ($C_1$–$C_4$)alkyl, ($C_1$–$C_4$)alkoxy, halogen or $CF_3$;

n is 0 or an integer from 1 to 6;

$R^2$ is hydrogen, —O($C_1$–$C_4$)alkyl, —O($C_3$–$C_7$)cycloalkyl or —O($CH_2$)$_n$phenyl where the phenyl portion is optionally substituted with ($C_1$–$C_4$)alkyl, ($C_1$–$C_4$)alkoxy, halogen or $CF_3$;

$R^3$ is hydrogen or ($C_1$–$C_4$)alkyl;

$R^4$ is hydrogen or ($C_1$–$C_4$)alkyl; and $R^5$ is hydrogen or ($C_1$–$C_4$)alkyl;

provided that when:

$R^1$, $R^3$, $R^4$, and $R^5$ are each hydrogen $R^2$ is not 3-O-cyclopentyl;

$R^3$, $R^4$, and $R^5$ are each hydrogen and $R^2$ is 3-OMe, $R^1$ is not 4-O-cyclopentyl; and $R^4$ and $R^5$ are each hydrogen, $R^3$ is ethyl, $R^1$ is 4-OMe, $R^2$ is not 3-O-($CH_2$)$_5$phenyl.

Further still, this invention is directed to a method of treating or alleviating an inflammatory disease or condition in a mammal in need thereof wherein the inflammatory disease or condition is asthma, arthritis, bronchitis, chronic obstructive pulmonary disease, psodasis, allergic rhinitis, dermatitis, shock, atopic dermatitis, rheumatoid arthritis or osteoarthritis which method comprises administering to said mammal an effective amount of a compound selected from the group consisting of compounds of the formula (I)

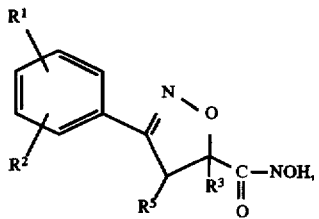

(I)

the racemic, racemic-diastereomeric mixtures and optical isomers of said compounds, and the pharmaceutically acceptable salts thereof, wherein $R^1$ is —O($C_1$–$C_4$)alkyl, —O($CH_2$)$_n$phenyl where the phenyl portion is optionally substituted with ($_1$–$C_4$)alkyl, ($C_1$–$C_4$)alkoxy, halogen or $CF_3$, or —O($CH_2$)$_n$quinoline where the quinoline is optionally substituted with ($C_1$–$C_4$)alkyl, ($C_1$–$C_4$)alkoxy, halogen or $CF_3$;

n is 0 or an integer from 1 to 6;

$R^2$ is hydrogen, —O($_1$–$C_4$)alkyl, —O($C_3$–$C_7$)cycloalkyl or —O($CH_2$)$_n$phenyl where the phenyl portion is optionally substituted with ($C_1$–$C_4$)alkyl, ($C_1$–$C_4$) alkoxy, halogen or $CF_3$;

$R^3$ is hydrogen or ($C_1$–$C_4$)alkyl;

$R^4$ is hydrogen or ($C_1$–$C_4$)alkyl; and $R^5$ is hydrogen or ($C_1$–$C_4$)alkyl;

provided that when:

$R^1$, $R^3$, $R^4$, and $R^5$ are each hydrogen $R^2$ is not 3-O-cyclopentyl;

$R^3$, $R^4$, and $R^5$ are each hydrogen and $R^2$ is 3-OMe, $R^1$ is not 4-O-cyclopentyl; and $R^4$ and $R^5$ are each hydrogen, $R^3$ is ethyl, $R^1$ is 4-OMe, $R^2$ is not 3-O-($CH_2$)$_5$phenyl.

In another aspect this invention provides pharmaceutical compositions comprising a compound selected from the group of compounds as defined directly above together with a pharmaceutically acceptable diluent or carrier which are useful in inhibiting 5-LO.

DETAILED DESCRIPTION OF THE INVENTION

The compounds utilized in the present invention, having the formula (I) as defined above, are readily and generally prepared by the following reaction process.

To an alcoholic solution of sodium methoxide is added an alcoholic solution of hydroxylamine hydrochloride and a compound of the formula

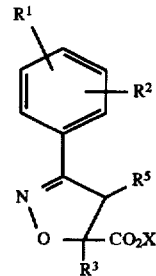

wherein X is an alkyl group and $R^1$, $R^2$, $R^3$ and $R^5$ are as defined for formula (I). The reaction mixture is stirred for about 12 to 24 hours, preferably 16 hours, at room temperature. The solvent is evaporated and the residue is worked-up according to methods well known to those skilled in the art.

The intermediate ester compounds of the formula

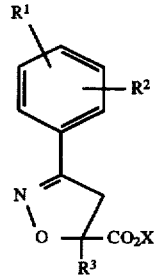

are synthesized according to the following procedure. To a mixture of N-chlorosuccinimide and pyridine in an inert solvent, such as methylene chloride, is added an oxime of the formula

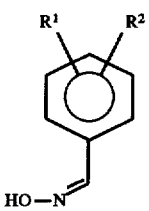

wherein $R^1$ and $R^2$ are as defined above for formula (I). The mixture is allowed to stir for about 2 to 5 hours, preferably about 2 hours. A compound of the formula

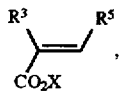

wherein $R^3$ and $R^5$ are as defined above for formula I and X is an alkyl group, is added followed by the addition of triethylamine to the mixture and the mixture is stirred for about 2 hours more at room temperature. The reaction is worked up according to methods well known to those skilled in the art.

Where possible, as ascertained by one skilled in the art enabled by this disclosure, pharmaceutically-acceptable acid addition salts of certain compounds of this invention can be prepared which include, but are not limited to, those formed with HCl, HBr, $HNO_3$, $H_2SO_4$, $H_3PO_4$, $CH_3SO_3H$, p-$CH_3C_6H_4SO_3H$, $CH_3CO_2H$, gluconic acid, tartaric acid, maleic acid and succinic acid.

The ability of the compounds or the pharmaceutically acceptable salts thereof to inhibit 5-LO and, consequently, demonstrate their effectiveness for treating or alleviating inflammatory diseases or conditions, allergy and cardiovascular diseases in mammals is shown by the following in vitro assay.

A23187-Induced Human Blood Leukotriene Release (5-LO)

Venous blood from healthy volunteers is collected in heparin (20 U/ml). Compounds are dissolved in DMSO. Each compound is tested at 4 concentrations. Zileuton (a 5-lipoxygenase inhibitor available from Abbott Laboratories, this particular batch was synthesized in house, the synthetic procedure is well-known in the art) and DMSO alone are used as positive and negative controls, respectively. 10 µl of compound or DMSO is added to glass borosilicate tubes (12×75 mm) and warmed to 37° C. One milliliter of whole blood is added to each tube. Following a 15 min. incubation period whole blood is stimulated with the calcium ionophore A23187 (purchased from Sigma Chemical Co., St. Louis, Mo. 63178), at 50 µM for 1 hour. Tubes are immediately placed in a 4C centrifuge and spun at 1500×g to isolate plasma. A 50 µl volume of plasma is taken for measurement of leukotriene-B4 (LTB4).

Samples are diluted 1:800 for assay by Leukotriene B4 Enzyme Immunoassay Kit (EIA) (Cayman Chemical Co., Ann Arbor, Mich.) using the manufacturers instructions. A LTB-4 standard curve from 250 to 7.8 pg/ml is run with each plate. 50 µl of diluted sample is added per well. 50 µl of LTB-4 acetylcholinesterase tracer followed by 50 µl of LTB-4 antiserum are then added. Plates are covered with plastic film and incubated for 18 hours at room temperature. Wells are emptied and rinsed 5 times with wash buffer prior to development with Ellman's Reagent (available from Cayman Chemical, Ann Arbor, Mich.) in the dark for 1 hour at room temperature, or until the B0 (total absorbance) wells exhibit absorbance between 0.3 and 0.8 A.U. The plates are read at 405 nm using a THERMOmax microplate reader (Molecular Devices, Menlo Park, Cal.).

The LTB-4 standard curve is fitted to a semi-log equation. Absorbance values for experimental wells are averaged and the pg/ml LTB-4 concentration is determined by interpolating the average absorbance onto the standard curve. Percent inhibition is determined by the following equation: (−|(pg/ml) LTB-4 experimental/(pg/ml) LTB-4 DMSO control|-1) ×100. $IC_{50}$ is determined by linear regression of drug concentration plotted against inhibition and interpolation of the x value at y=50.

For administration to humans to inhibit 5-LO and in the treatment of inflammatory diseases or conditions, allergy and cardiovascular diseases, oral dosages of the compounds of formula (I) or the pharmaceutically acceptable salts thereof, are generally in the range of from 0.1–500 mg daily for an average adult patient (70 kg). Thus for a typical adult patient, individual tablets or capsules contain from 0.1 to 50 mg of active compound, in a suitable pharmaceutically acceptable vehicle or carrier. Multiple tablets or capsules may be required to meet the dosage requirements. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For human use, the compounds of the formula (I) and the pharmaceutically acceptable salts thereof can be administered alone, but will generally be administered in an admixture with a pharmaceutical diluent or carrier selected with regard to the intended mute of administration and standard pharmaceutical practice. For example, they may be administered orally in the form of tablets containing such excipients as starch or lactose, or in capsules or ovales either alone or in admixture with excipients, or in the form of elixirs or suspensions containing flavoring or coloring agents. They may be injected parenterally; for example, intravenously, intramuscularly or subcutaneously. For parenteral administration, they are best used in the form of a sterile aqueous solution which may contain other substances; for example, enough salts or glucose to make the solution isotonic. For topical administration, they are best used in the form of solutions, lotions, ointments, salves and the like.

The following example illustrates the synthesis of a compound used in the present invention. The following example combined with the synthetic methodologies described immediately above enables one skilled in the art to prepare the compounds used in the present invention.

EXAMPLE 1

3-(3-Cyclopentyloxy-4-methoxy)phenyl-2-isoxazoline-5-hydroxamic Acid

To a solution of sodium methoxide, prepared from 97 mg (4.2 mmol) of sodium and 10 ml of methanol, was added 146 mg (2.1 mmol) of hydroxylamine hydrochloride in a solution of 3 ml of methanol followed by 500 mg (1.5 mmol) of 3-(3-cyclopentyoxy-4-methoxy)phenyl-2-isoxazoline-5-carboxylic acid ethyl ester. After stirring for about 16 h at RT, the solvent was evaporated and the residue was dissolved in 50 ml of water and washed with ether (2×50 ml). The aqueous layer was acidified to pH 1 with aqueous HCl solution and the precipitate (231 mg) was filtered and recrystallized twice from $CH_2Cl_2$ EtOAc to give 52 mg of the title compound, mp 167°–168° C. $^1H$ NMR (DMSO-$d_6$): δ1.54–1.92 (8H, m), 3.48–3.67 (2H, m), 3.78 (3H, s), 4.79–4.85 (1H, m), 4.95 (1H, t, J=8), 6.99 (1H, d, J=9), 7.17 (1H, d, J=9), 7.23 (1H, s), 9.03 (1H, s); Anal. Calc'd. for $C_{16}H_{20}N_2O_5$: C, 59.99; H, 6.29; N, 8.74. Found: C, 59.82; H, 6.05; N, 8.65.

What is claimed is:

1. A method of inhibiting production of 5-lipoxygenase in a mammal in need thereof which method comprises administering to said mammal an effective amount of a compound selected from the group consisting of compounds of the formula (I)

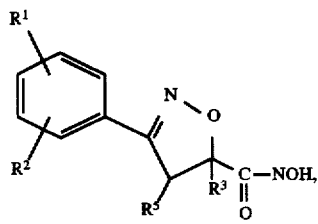

the racemic, racemic-diastereomeric mixtures and optical isomers of said compounds, and the pharmaceutically acceptable salts thereof, wherein $R^1$ is —$O(C_1-C_4)$alkyl, —$O(CH_2)_n$phenyl where the phenyl portion is optionally substituted with $(C_1-C_4)$alkyl, $(C_1-C_4)$alkoxy, halogen or $CF_3$, or —$O(CH_2)_n$quinoline where the quinoline is optionally substituted with $(C_1-C_4)$alkyl, $(C_1-C_4)$alkoxy, halogen or $CF_3$;

n is 0 or an integer from 1 to 6;

$R^2$ is hydrogen, —$O(C_1-C_4)$alkyl, —$O(C_3-C_7)$cycloalkyl or —$O(CH_2)_n$phenyl where the phenyl portion is optionally substituted with $(C_1-C_4)$alkyl, $(C_1-C_4)$alkoxy, halogen or $CF_3$;

$R^3$ is hydrogen or $(C_1-C_4)$alkyl;

$R^4$ is hydrogen or $(C_1-C_4)$alkyl; and $R^5$ is hydrogen or $(C_1-C_4)$alkyl;

provided that when:

$R^1$, $R^3$, $R^4$, and $R^5$ are each hydrogen $R^2$ is not 3-O-cyclopentyl;

$R^3$, $R^4$, and $R^5$ are each hydrogen and $R^2$ is 3-OMe, $R^1$ is not 4-O-cyclopentyl; and $R^4$ and $R^5$ are each hydrogen, $R^3$ is ethyl, $R^1$ is 4-OMe, $R^2$ is not 3-O-$(CH_2)_5$phenyl.

2. A method of inhibiting production of 5-lipoxygenase in a mammal in need thereof according to claim 1 wherein $R^1$ is 4-OMe, 4-O-$CH_2$-phenyl or 4-O-$CH_2$-2-quinoline;

$R^2$ is hydrogen, 3-O-cyclopentyl or 3-O$(CH_2)_5$phenyl;

$R^3$ is hydrogen, methyl or ethyl;

$R^4$ is hydrogen or methyl; and $R^5$ is hydrogen.

3. A method of treating or alleviating an inflammatory disease or condition, allergy or cardiovascular disease in a mammal in need thereof which method comprises administering to said mammal an effective amount of a compound selected from the group consisting of compounds of the formula (I)

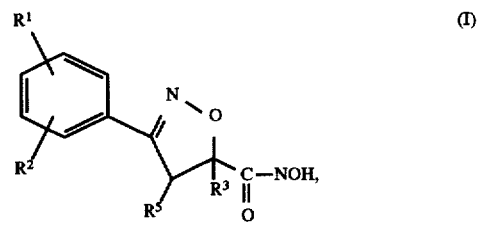

the racemic, racemic-diastereomeric mixtures and optical isomers of said compounds, and the pharmaceutically acceptable salts thereof, wherein $R^1$ is —$O(C_1-C_4)$alkyl, —$O(CH_2)_n$phenyl where the phenyl portion is optionally substituted with $(C_1-C_4)$alkyl, $(C_1-C_4)$alkoxy, halogen or $CF_3$, or —$O(CH_2)_n$quinoline where the quinoline is optionally substituted with $(C_1-C_4)$alkyl, $(C_1-C_4)$alkoxy, halogen or $CF_3$;

n is 0 or an integer from 1 to 6;

$R^2$ is hydrogen, —$O(C_1-C_4)$alkyl, —$O(C_3-C_7)$cycloalkyl or —$O(CH_2)_n$phenyl where the phenyl portion is optionally substituted with $(C_1-C_4)$alkyl, $(C_1-C_4)$alkoxy, halogen or $CF_3$;

$R^3$ is hydrogen or $(C_1-C_4)$alkyl;

$R^4$ is hydrogen or $(C_1-C_4)$alkyl; and $R^5$ is hydrogen or $(C_1-C_4)$alkyl;

provided that when:

$R^1$, $R^3$, $R^4$, and $R^5$ are each hydrogen $R^2$ is not 3-O-cyclopentyl;

$R^3$, $R^4$, and $R^5$ are each hydrogen and $R^2$ is 3-OMe, $R^1$ is not 4-O-cyclopentyl; and $R^4$ and $R^5$ are each hydrogen, $R^3$ is ethyl, $R^1$ is 4-OMe, $R^2$ is not 3-O-$(CH_2)_5$phenyl.

4. A method according to claim 3 wherein the inflammatory disease or condition is asthma, arthritis, bronchitis, chronic obstructive pulmonary disease, psoriasis, allergic rhinitis, dermatitis, shock, atopic dermatitis, rheumatoid arthritis or osteoarthritis.

* * * * *